United States Patent
Lee et al.

(10) Patent No.: US 7,912,537 B2
(45) Date of Patent: Mar. 22, 2011

(54) TELEMETRY-SYNCHRONIZED PHYSIOLOGICAL MONITORING AND THERAPY DELIVERY SYSTEMS

(75) Inventors: Brian B. Lee, Golden Valley, MN (US); Eric J. Panken, Edina, MN (US); Can Cinbis, Shoreview, MN (US); Gerard J. Hill, Champlin, MN (US); John J. Grevious, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 450 days.

(21) Appl. No.: 11/380,435

(22) Filed: Apr. 27, 2006

(65) Prior Publication Data
US 2007/0255330 A1 Nov. 1, 2007

(51) Int. Cl.
*A61N 1/06* (2006.01)

(52) U.S. Cl. ............... 600/547; 607/9; 607/60; 128/903

(58) Field of Classification Search .............. 607/60
See application file for complete search history.

(56) References Cited

U.S. PATENT DOCUMENTS

| | | | |
|---|---|---|---|
| 4,987,897 A | 1/1991 | Funke | |
| 5,113,859 A | 5/1991 | Funke | |
| 5,211,173 A | 5/1993 | Kallok et al. | |
| 5,701,894 A | 12/1997 | Cherry et al. | |
| 5,876,353 A * | 3/1999 | Riff | 600/547 |
| 5,987,352 A | 11/1999 | Klein et al. | |
| 5,995,868 A | 11/1999 | Dorfmeister et al. | |
| 6,061,593 A * | 5/2000 | Fischell et al. | 600/544 |
| 6,132,384 A | 10/2000 | Christopherson et al. | |
| 6,134,474 A * | 10/2000 | Fischell et al. | 607/45 |
| 6,138,044 A | 10/2000 | Svedman | |
| 6,159,156 A * | 12/2000 | Van Bockel | 600/485 |
| 6,354,299 B1 * | 3/2002 | Fischell et al. | 128/899 |
| 6,572,542 B1 | 6/2003 | Houben et al. | |
| 6,599,242 B1 | 7/2003 | Splett et al. | |
| 6,647,296 B2 * | 11/2003 | Fischell et al. | 607/45 |
| 7,155,284 B1 * | 12/2006 | Whitehurst et al. | 607/44 |
| 7,203,548 B2 * | 4/2007 | Whitehurst et al. | 607/39 |
| 7,292,890 B2 * | 11/2007 | Whitehurst et al. | 607/45 |
| 2002/0002390 A1 * | 1/2002 | Fischell et al. | 607/45 |
| 2002/0024450 A1 * | 2/2002 | Townsend et al. | 340/870.16 |
| 2002/0082658 A1 | 6/2002 | Heinrich et al. | |
| 2004/0015204 A1 * | 1/2004 | Whitehurst et al. | 607/48 |

(Continued)

FOREIGN PATENT DOCUMENTS

EP 0356603 3/1990

(Continued)

OTHER PUBLICATIONS

Stein, R.B. et al. "Stimulation of peripheral nerves with a microstimulator: experimental results and clinical application to correct foot drop"; 9th Annual Conference of the International FES Society, Sep. 2004.

(Continued)

*Primary Examiner* — Carl H. Layno
*Assistant Examiner* — Jon-Eric C. Morales
(74) *Attorney, Agent, or Firm* — Michael J. Ostrom; Stephen W. Bauer

(57) ABSTRACT

A physiological monitoring or therapy delivery system includes autonomous, wirelessly linked, implantable devices located at different areas to sense physiologic signals and deliver therapy. At least one of the implantable devices can trigger synchronized action (e.g. data capture or therapy delivery) by other implantable devices via a telemetry link.

20 Claims, 6 Drawing Sheets

U.S. PATENT DOCUMENTS

| | | | |
|---|---|---|---|
| 2004/0015205 A1* | 1/2004 | Whitehurst et al. | 607/48 |
| 2004/0049120 A1 | 3/2004 | Cao et al. | |
| 2004/0138721 A1* | 7/2004 | Osorio et al. | 607/45 |
| 2004/0220626 A1 | 11/2004 | Wagner | |
| 2005/0107838 A1 | 5/2005 | Lovett et al. | |
| 2005/0115561 A1* | 6/2005 | Stahmann et al. | 128/200.24 |
| 2005/0165458 A1* | 7/2005 | Boveja et al. | 607/45 |
| 2005/0182389 A1 | 8/2005 | LaPorte et al. | |
| 2006/0135877 A1* | 6/2006 | Giftakis et al. | 600/513 |
| 2006/0135881 A1* | 6/2006 | Giftakis et al. | 600/544 |
| 2006/0136006 A1* | 6/2006 | Giftakis et al. | 607/45 |
| 2006/0195039 A1* | 8/2006 | Drew et al. | 600/523 |
| 2006/0195144 A1* | 8/2006 | Giftakis et al. | 607/2 |
| 2006/0224067 A1* | 10/2006 | Giftakis et al. | 600/483 |
| 2007/0021800 A1* | 1/2007 | Whitehurst et al. | 607/45 |
| 2007/0255147 A1* | 11/2007 | Drew et al. | 600/509 |
| 2007/0255155 A1* | 11/2007 | Drew et al. | 600/523 |
| 2007/0255531 A1* | 11/2007 | Drew | 702/189 |
| 2007/0265508 A1* | 11/2007 | Sheikhzadeh-Nadjar et al. | 600/300 |
| 2007/0282210 A1* | 12/2007 | Stern | 600/486 |
| 2008/0033490 A1* | 2/2008 | Giftakis et al. | 607/2 |
| 2008/0065183 A1* | 3/2008 | Whitehurst et al. | 607/116 |

FOREIGN PATENT DOCUMENTS

| | | |
|---|---|---|
| WO | WO9802209 | 1/1998 |
| WO | WO9934724 | 7/1999 |
| WO | WO02051497 | 7/2002 |
| WO | WO2005028029 | 3/2005 |

OTHER PUBLICATIONS

Shulman, J.H. et al. "Battery Powered BION FES Network"; 26th Annual International Conference of the IEEE EMBS, Sep. 2004, 4283-4286.

Burridge, J. et al. "Long-term follow-up of patients using the ActiGait implanted drop-foot stimulator"; 10th Annual Conference of the International FES Society, Jul. 2005.

Kenney, L. et al. "An Implantable Two Channel Drop Foot Stimulator: Initial Clinical Results"; Artificial Organs, 26(3), 267-270, International Society for Artificial Organs, 2002.

Kenney, L. "Recent advances in FES and AFO technology"; FES and AFO Workshop, University of Salford, Sep. 2005.

International Search Report, PCT/US2007/067271, Nov. 23, 2007, 7 Pages.

* cited by examiner

TELEMETRY-SYNCHRONIZED PHYSIOLOGICAL MONITORING AND THERAPY DELIVERY SYSTEMS

REFERENCE TO COPENDING APPLICATIONS

Reference is made to the following co-pending applications: Ser. No. 11/311,043 filed Dec. 19, 2005; Ser. No. 11/311,200 filed Dec. 19, 2005; Ser. No. 11/311,393 filed Dec. 19, 2005; and Ser. No. 11/311,456 filed Dec. 19, 2005, each of which claims priority from Ser. No. 60/636,929 filed Dec. 17, 2004. Each of these referenced applications is hereby incorporated by reference.

BACKGROUND OF THE INVENTION

This invention relates to implantable medical devices (IMDs) for sensing physiological signals, monitoring and recording physiological events, and delivering therapy. In particular, the invention relates to telemetry-synchronized operation of multiple IMDs.

Pacemakers, cardioverter defibrillators, nerve stimulators, and drug delivery devices are examples of IMDs used to provide therapy over extended periods of time to a patient. These devices typically include sensors that are located on or in the IMD housing or are connected to the IMD by electrical leads. The IMD includes signal processing circuitry for processing physiologic signals from the sensors, and therapy delivery circuitry for controlling the delivery of therapy based upon the sensed physiologic signals. The therapy may include electrical stimulation of nerves, muscles, organs, or may be the delivery of therapeutic substances such as insulin or drugs.

The monitoring and recording of physiologic events in a patient's body over extended periods of time has important diagnostic, therapeutic, and research benefits. Ambulatory recorders have been developed for electrocardiogram (ECG), electroencephalogram (EEG), blood pressure, and other physiologic signals. Both externally worn monitors and implantable monitors have been developed. For example, the Klein et al. U.S. Pat. No. 5,987,352 describes an implantable long term ECG monitor that automatically detects arrhythmia and records ECG signals in memory. The recorded ECG signals can later be transferred by telemetry to an external device.

The human body is a complex organism with many inter-related systems. A physiologic condition may manifest itself concurrently or sequentially at different places in the body. Improved diagnosis and treatment may be aided by capturing data and delivering therapy based upon sensed physiologic signals from different portions of the body.

BRIEF SUMMARY OF THE INVENTION

A system of autonomous implantable medical devices uses an inter-device telemetry link to trigger synchronized action. A physiologic event within a first region of a patient's body, or an external device activation, sensed by a first IMD can trigger a synchronized action by a second IMD that interacts with a second region of a patient's body.

The telemetry-synchronized system can be used to provide synchronized data capture, sensing, or therapy delivery involving implantable medical devices located in different parts of the body. Telemetry-synchronized operation of autonomous IMDs is particularly useful when sensing or therapy delivery occur in locations within the body that are distant from one another so that it is undesirable to provide physical links between the IMDs for communication or transfer/delivery of energy or drugs.

DETAILED DESCRIPTION

Figure 1A:
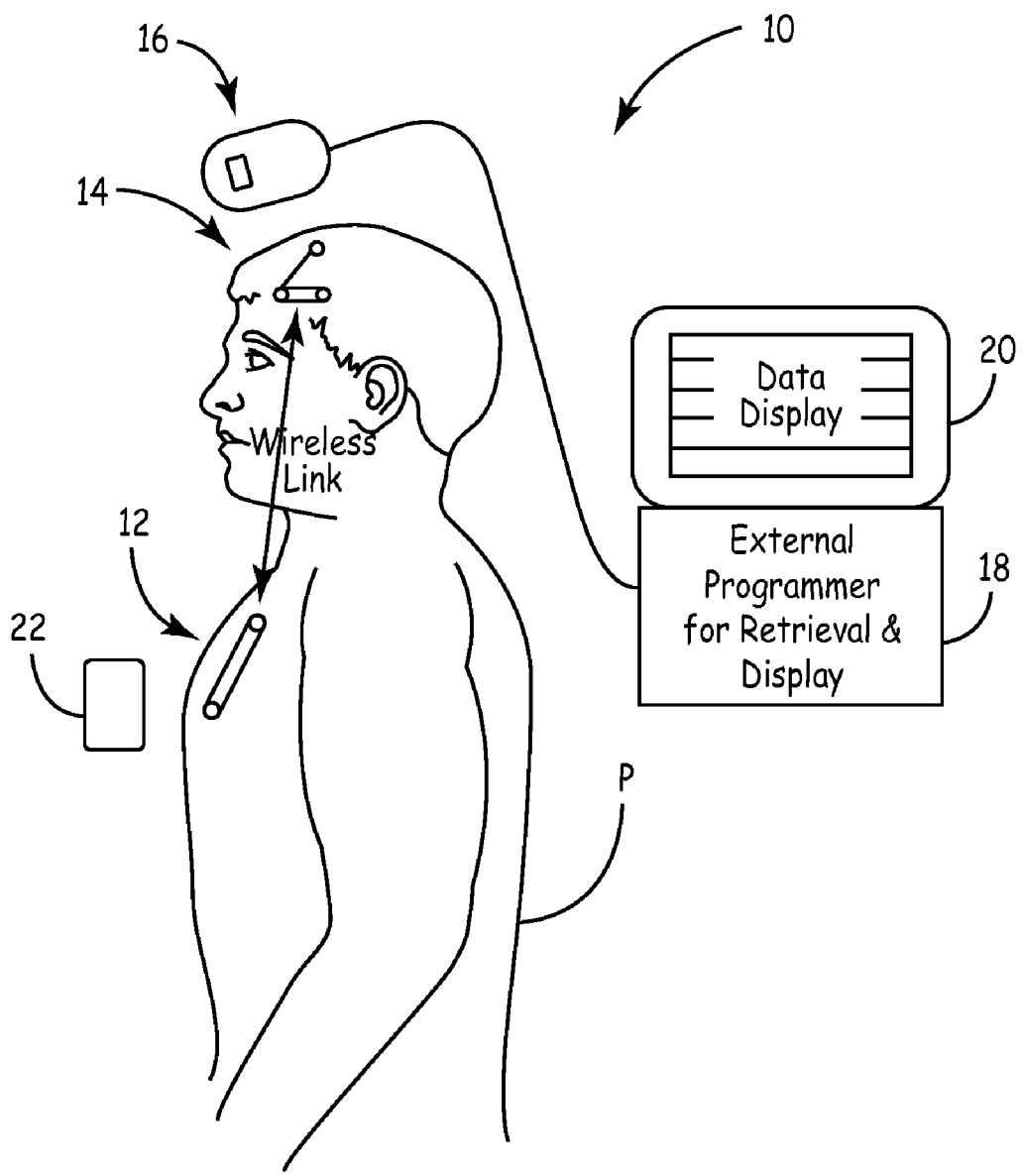
FIG. 1A shows a telemetry-synchronized monitoring system including implantable ECG and EEG monitors.

FIG. 1A shows seizure/syncope monitoring system 10, which includes implantable ECG monitor 12, implantable EEG monitor 14, external telemetry head 16, external programmer 18, data display 20, and patient-carried wireless activator 22, which the patient can use to communicate to the implant(s) to trigger the capture of symptomatic data. Monitoring system 10 is used to help diagnose and monitor infrequent syncopal/seizure patients by using two chronically implantable autonomous, wirelessly-linked devices: ECG monitor 12 and EEG monitor 14.

ECG monitor 12 is implanted in the chest region of patient P, and includes electrodes and signal processing circuitry for sensing ECG signals and detecting cardiac arrhythmias. An example of an implantable ECG monitor is the Medtronic Reveal Plus® Insertable Loop Recorder.

EEG monitor 14 includes electrodes and signal processing circuitry for sensing EEG signals representing electrical activity of the brain and detecting seizures based upon the EEG signals.

Both ECG monitor 12 and EEG monitor 14 include memory for storing sensed physiological signals, and internal clocks for providing time stamps in conjunction with the stored data. Monitors 12 and 14 can generate a trigger signal automatically based upon a detected event, or based on a trigger signal received by telemetry from the other monitor. Patient P can also trigger simultaneous capture of EEG and ECG data by placing patient activator 22 near either EEG monitor 14 or ECG monitor 12 and transmitting a trigger signal. Both monitors 12 and 14 may receive the trigger signal and initiate simultaneous data capture, or one monitor may receive the trigger signal from patient activator 22 and relay the trigger wirelessly to the other monitor.

In the embodiment shown in FIG. 1A, synchronized data acquisition is achieved with implanted ECG monitor 12 and implanted EEG monitor 14. When one device senses an event to be recorded, it sends a telemetry signal to the other device to initiate data storage during the recorded event. This type of intra body telemetry requires good transmitters and receivers. Transmit power should be high enough to be able to propagate the signal through the tissue of a patient's body to the other device. The signal-to-noise ratio of the receiver needs to be high enough so that the received signal is not corrupted.

Upon detecting an arrhythmia or detecting an external patient activation, ECG monitor 12 transmits a trigger signal via a wireless link to EEG monitor 14 to trigger simultaneous capture of EEG data. Conversely, upon detecting a seizure event or by external patient activation, EEG monitor 14 will provide a wireless trigger signal to ECG monitor 12 to trigger simultaneous capture of ECG data.

External telemetry head 16, together with external programmer 18, can retrieve the recorded data from both monitors 12 and 14, and display them in parallel on data display 20 for diagnosis. The clock values (e.g. a real time stamp or a clock count) recorded by both monitors 12 and 14 as a result of a trigger used to synchronize the captured EEG and ECG data allow the data to be viewed in parallel.

The wireless link between monitors 12 and 14 provides a simple wireless communication with the goal of synchronizing recording of ECG and EEG data. Since continuous transmission is not required, the instantaneous power of wireless transmission can be high, while the average continuous current is low, because episodes of arrhythmias and seizures are infrequent.

In the past, there has been no long-term diagnostic method for capturing both ECG and EEG data during infrequent symptomatic events such as vasovagal syncope and seizures. Thus, there has not been a reliable diagnostic method to distinguish between an event in which a seizure leads to cardiac arrhythmia, and an event in which cardiac arrhythmia results in syncope and an associated seizure-like behavior. In many patients, the spells of syncope or seizure-like behavior are too infrequent for short term monitoring methods to be effective.

System 10 provides synchronized simultaneous recording of EEG and ECG signals during symptomatic events such as syncope and/or seizures to help identify the underlying causes of the patient's symptoms. To the extent that the cardiac arrhythmias are a primary cause of infrequent symptomatic events, the effectiveness and side effects of anti-seizure medications for the patient can be evaluated.

Another issue with patients having infrequent syncopal/seizure events is a high incidence of sudden death, referred to as sudden death in epilepsy patients or SUDEP. Simultaneous capture of ECG and EEG data during arrhythmia may provide important diagnostic and research information regarding SUDEP.

The use of separate implantable monitors 12 and 14 allows each IMD to be small and easy to implant in the particular area where the physiological signal of interest (ECG or EEG) can be easily measured. In contrast, the use of a single IMD would require that all circuitry be contained in a single housing, and that leads be tunneled between the head and the chest, through the neck region.

Figure 1B:
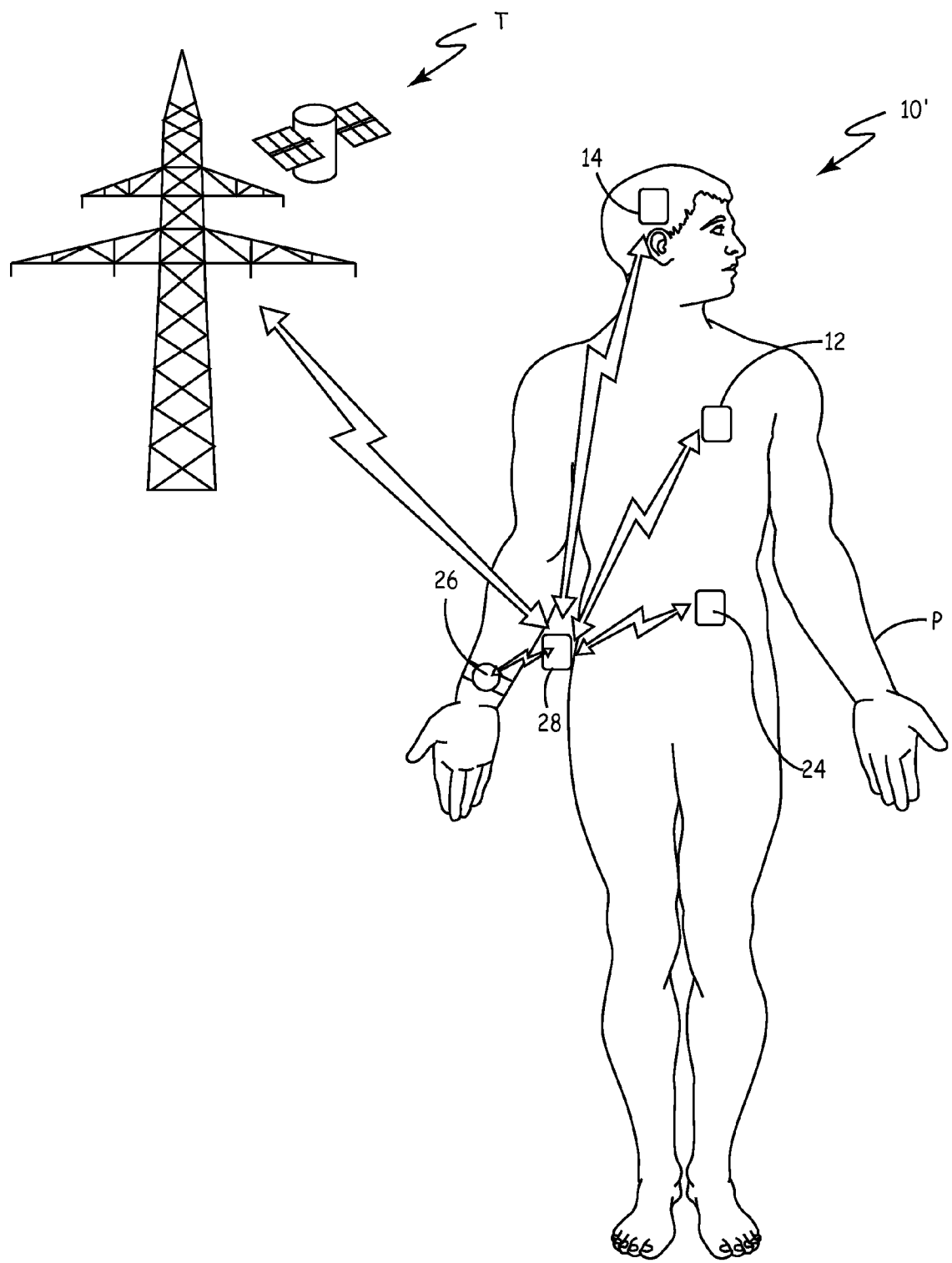
FIG. 1B shows a telemetry-synchronized monitoring system including implantable monitors and an external relay unit.

FIG. 1B shows another embodiment including ECG monitor 12 and EEG monitor 14, together with implanted aortic aneurysm monitor 24, wristwatch physiologic sensor 26, and pager 28. System 10' uses an externally wearable relay unit (in this case pager 28) to communicate with and synchronize the operation of monitors 12, 14, 24, and 26.

Because pager 28 is an externally wearable unit, additional complexity needed to provide a low noise receiver and a high power transmitter can more easily be achieved than with implantable devices. Power consumption of implantable monitors 12, 14, and 24 is reduced by the use of an external relay device such as pager 28.

Upon receiving an event trigger signal from any one of monitors 12, 14, 24, or 26, pager 28 can transmit data acquisition start triggers for all of the monitors at once. Pager 28 can also contain memory for storing data received from monitors 12, 14, 24, and 26, as well as wireless links to data networks, such as WI-FI or cell phones. Pager 28 can also contain electronics to receive accurate clock signals, such as from GPS, and update the clocks of monitors 12, 14, 24, and 26 on a periodic basis.

As shown in FIG. 1B, pager 28 communicates with wireless tower T to send data gathered by monitors 12, 14, 24, and 26 for review and analysis by medical personnel. Although in FIG. 1B pager 28 acts as the externally wearable relay unit, other devices can be used to perform the relay function. For example, a wristwatch monitor 26 can be configured to perform the relay function. The external relay unit could also be in the form of a pendant connected to a necklace. The external relay unit (i.e. pager 28) can also include an additional physiologic sensor within its housing to augment the monitoring of patient P.

Figure 2:
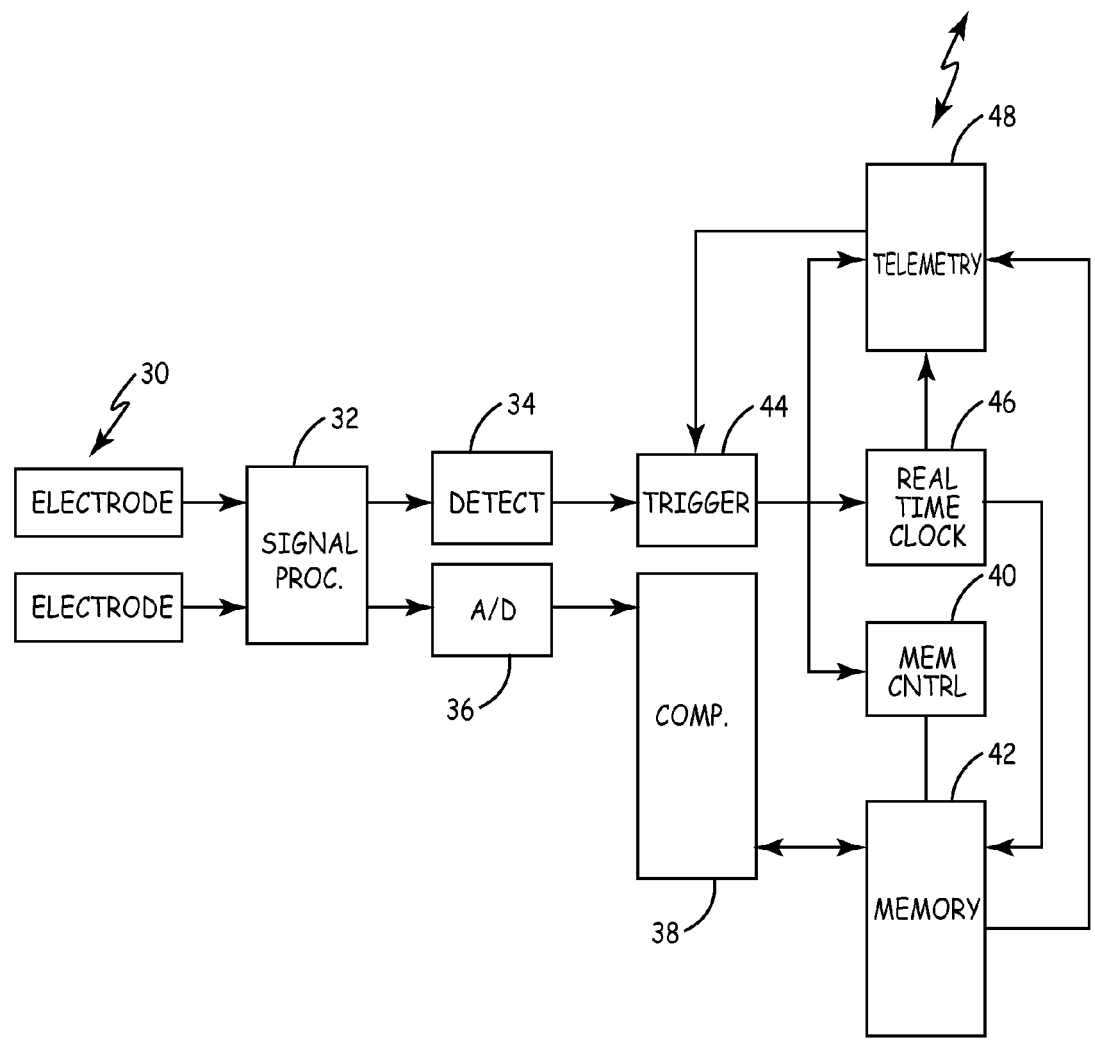
FIG. 2 is a block diagram of an example of an implantable monitor for use in the systems of FIGS. 1A and 1B.

FIG. 2 shows a block diagram of representative circuitry of an implantable monitor, such as ECG monitor 12 or EEG monitor 14. The circuitry includes sensing electrodes 30, signal processing circuitry 32, event detection circuit 34, analog-to-digital (A/D) converter 36, data compression circuit 38, memory control 40, memory 42, trigger circuit 44, real time clock 46, and telemetry 48.

Physiologic signals representing ECG activity (in the case of ECG monitor 12) or EEG activity (in the case of EEG monitor 14) are sensed by electrodes 30. For ECG monitor 12, electrodes 30 may be any number of electrodes (at least 2) carried on the outer surface near opposite ends of the housing of monitor 12 or short leads extending from the housing carrying one or more electrodes. EEG monitor 14 may have a similar arrangement of electrodes on its housing, or may also include a lead (or leads) extending from the housing and carrying one or more EEG electrodes. These EEG electrodes can be located in the subcutaneous space or implanted through the skull into the dura space to provide better signal amplitude and quality.

Signal processing circuitry 32 amplifies and filters the physiologic signals received from electrodes 30. The output of signal processing circuitry 32 is provided to detection circuitry 34 and to A/D converter 36. Detection circuitry 34 provides signal analysis of the physiologic signals for detecting a physiologic event. In the case of ECG monitor 12, detection circuitry 34 detects the QRS complex of the ECG signals, and determines heart rate, which is then used to detect cardiac arrhythmia. ECG monitor 12 also uses morphological features to detect abnormalities, such as S-T segment elevation. In the case of EEG monitor 14, detection circuitry 34 analyzes the EEG signals in order to detect a seizure event.

The physiologic signal (ECG or EEG) is converted to digital form by A/D converter 36 and may be compressed by compression circuitry 38 for storage in memory 42. Because storage is limited, a looping memory organization may be used for storing and rewriting data, so that only data corresponding to detected events is retained in memory 42. A description of a method of storing data in a looping memory structure is found in the Klein et al. U.S. Pat. No. 5,987,352.

Upon detection of a physiologic event, detection circuit 34 provides a detection input to trigger circuit 44. The output of trigger circuit 44 is a trigger signal that is provided to memory control 40, real time clock 46, and telemetry 48.

The trigger signal from trigger circuit 44 is used by memory control 42 to define data within memory 42 stored before and after the trigger event that will be retained for later transmission to telemetry head 16 and external programmer 18. The trigger signal also causes real time clock 46 to provide to memory 42 a clock value indicating the time or clock count at which the trigger signal occurred.

The trigger signal from trigger circuit 44 is supplied to telemetry circuit 48, and is transmitted to the other monitor in order to synchronize data capture between monitors 12 and 14. When a telemetry-delivered trigger is received from an external source (i.e. either the other monitor or patient activator 22), trigger circuit 44 supplies a trigger signal to real time clock 46 and memory circuit 40. This causes storage and retention of data in memory 42, along with a time stamp or clock count indicating when the telemetry-delivered trigger was received.

Later, data is retrieved from ECG monitor 12 and EEG monitor 14 using external telemetry head 16 (FIG. 1A), pager 28 (FIG. 1B), or another external telemetry device. At that time, data is retrieved from memory 42 and is supplied by telemetry circuit 48 to the external device. In addition, the current time of transmission (or clock count) is supplied by real time clock 46 and transmitted by telemetry circuit 48.

External programmer 18 (or another external device that receives the data) can determine the time at which the trigger event corresponding to the captured data occurred by using clock value (the time stamp or clock count) at the time of the trigger event, and the clock value at the time of transmission of the data as well as the time indicated by a real time clock of external programmer 18. By knowing the clock value at time of transmission, the corresponding real time and the clock frequency of monitor 12 or 14, external programmer can calculate the time of the event based on the trigger event clock value. After data has been retrieved from one monitor, external telemetry head 16 is placed near the other monitor to repeat the data retrieval process.

When the data retrieval is complete, each of the monitors 12 and 14 will have provided its captured data with a trigger time stamp, together with the time of transmission (and also possibly via an event ID transmitted from one device to the other at the time of the synchronized trigger). With that information, external programmer 18 can correlate the data, so that EEG and ECG data corresponding to the same trigger event can be displayed in a time-correlated fashion on data display 20.

Systems 10 and 10' do not require that the real-time clocks 46 of monitor 12 and 14 be synchronized via a common clock. Rather, it is only necessary that time of the events by tracked by the separate monitors accurately enough to correlate the events (generally within several minutes will suffice). Alternatively, event ID's could be passed from device-to-device on the triggers and kept with the events to correlate them later. In that case, the correlation is done independent of the clocks themselves. It is important that each monitoring device in conjunction with the retrieval times as indicated by external programmer 18, keep track of the time of events to within minutes of the event to help correlate to the symptoms remembered by patient P.

Another application of telemetry-synchronized operation of multiple IMDs provides synchronized therapy in response to a detected physiologic event, rather than data capture. The synchronized therapy can be any type of stimulus that affects an organ, tissues, or nerves. Examples of stimuli produced in response to a telemetry trigger include electrical, thermal, optical, chemical, mechanical, or magnetic stimuli. Telemetry-synchronized operation of IMDs for therapy delivery can be used to synchronize any physiologic function occurring remotely that is not being controlled by normal synchronizing body signals (e.g. neuropaths or neuro-hormonal signals in the bloodstream), or by physical relationships (e.g. breathing muscle movement causing pressure drops in the chest, pulling air through the pharynx).

Figure 3:
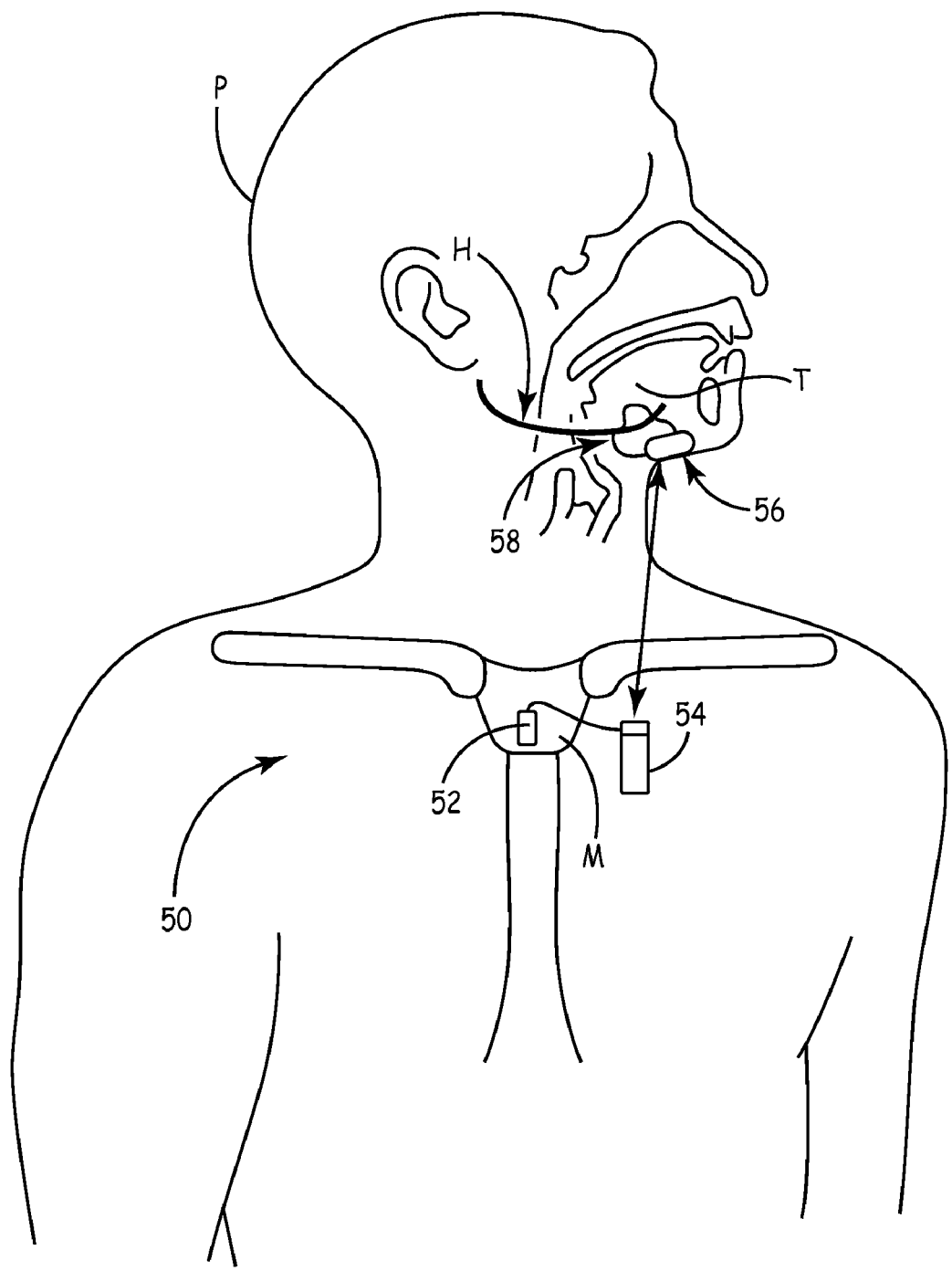
FIG. 3 shows a telemetry-synchronized system for treating obstructive sleep apnea.

An example of telemetry-synchronized therapy delivery is sleep apnea treatment system 50, shown in FIG. 3. System 50 includes respiration sensor 52, implantable sensor detector 54, implantable stimulator 56, and stimulator lead 58. System 50 provides treatment for obstructive sleep apnea by sensing a characteristic of respiratory effort, detecting an event based upon the sensed respiratory effort characteristic, producing a wireless trigger signal based upon the detected event, and providing inspiration synchronized stimulation in response to the trigger signal.

Respiration sensor 52 is surgically implanted in the chest wall near the lungs, and is connected by lead 60 to inspiration detector 54. Respiration sensor 52 may be, for example, a pressure sensor placed just below the dicrotic notch in manubrium M.

Signal processing circuitry and detection logic of inspiration detector 54 processes the respiratory effort signal produced by respiration sensor 52. Based upon the respiratory effort signal, inspiration detector 54 produces a trigger signal having a synchronized relationship to the onset of inspiration. Inspiration detector 54 transmits the trigger signal by a wireless synchronizing link to stimulator 56.

As shown in FIG. 3, stimulator 56 is implanted in or near the base of tongue T. In response to the wireless trigger signal, stimulator 56 produces an electrical stimulus that is delivered through stimulator lead 58 to hypoglossal nerve H. The stimulus causes tongue T to be pulled forward to avoid an apnea event.

System 50 operates in a manner similar to the sleep apnea treatment system described in the Christopherson et al. U.S. Pat. No. 6,132,384. System 50, however, uses two implantable devices (inspiration detector 54 and stimulator 56) rather than a single implantable pulse generator as described in the Christopherson et al. patent. By using two small implantable devices and a wireless synchronizing link, the tunneling of leads through the neck region of patient P is avoided.

Figure 4:
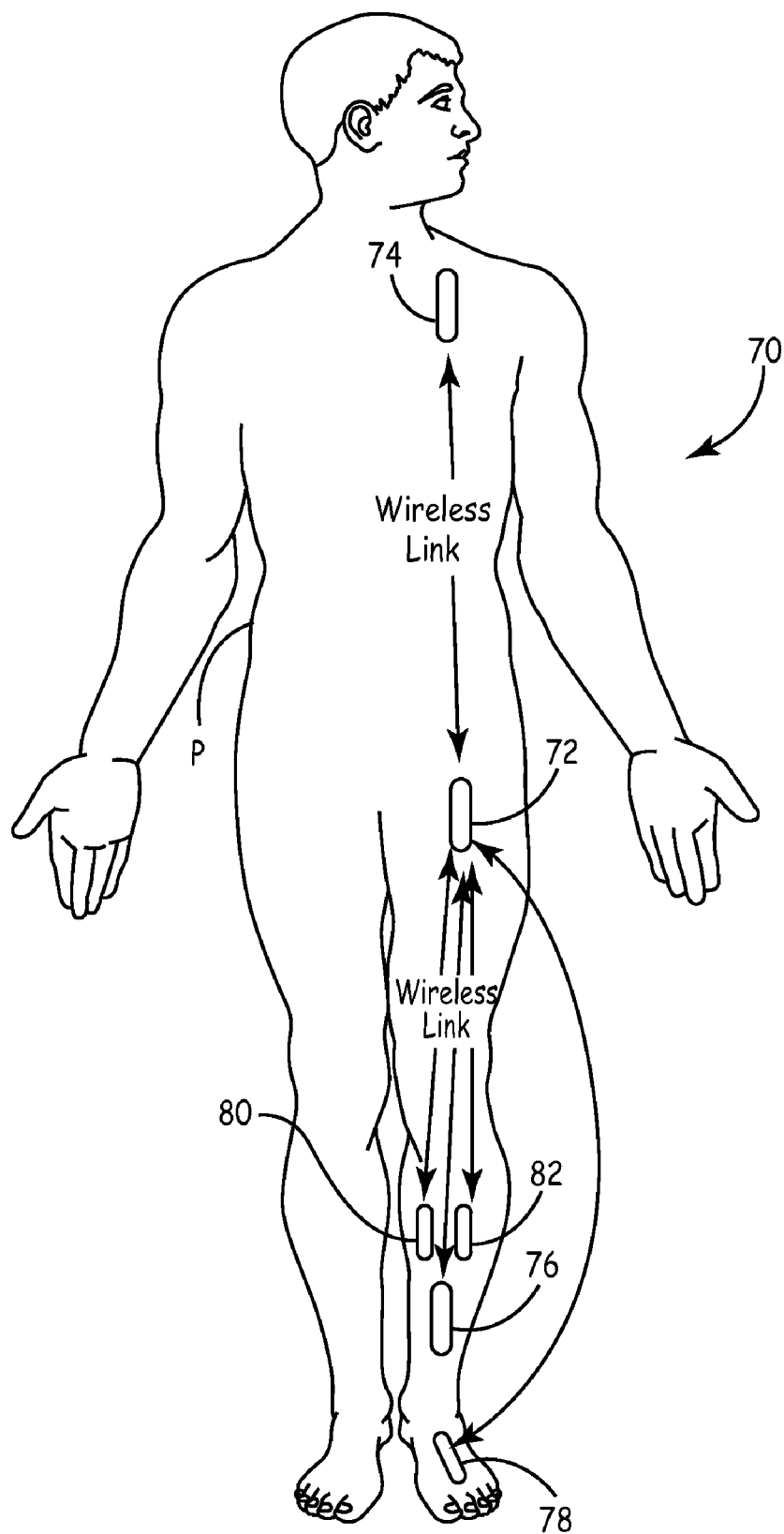
FIG. 4 is a diagram showing a telemetry-synchronized leg control system.

FIG. 4 shows another implementation of telemetry synchronization of IMDs timed to provide staggered delivery of therapy to organs, tissues, or nerves. FIG. 4 shows an example of telemetry-synchronized therapy with leg control system 70 used to help a paralyzed person (e.g. a stroke victim) walk.

Leg control system 70 includes as many as six implanted devices interconnected with wireless links. Sensor/controller 72 is implanted in the upper leg region, sensor 74 is implanted in the chest, sensor 76 is implanted in the lower leg above the ankle, and sensor 78 is implanted in the foot. Sensors 72, 74, 76, and 78 may be accelerometers that provide outputs related to orientation or inclination of particular parts of the body. Stimulators 80 and 82 are implanted in the lower leg on or near the deep peroneal and superficial peroneal nerves to provide drop foot stimulation. Deep peroneal nerve stimulation controls muscles that lift and invert the foot, while superficial peroneal nerve stimulation controls muscles that evert the foot.

Sensor/controller 72 acts as the master control for leg control system 70. Sensor/controller 72 detects an urge to walk by sensing when the upper leg is elevated. Sensor/controller 72 receives wireless signals from sensors 74, 76, and 78 indicating body posture, lower leg orientation and foot orientation. Sensor/controller 72 provides wireless trigger signals to stimulators 80 and 82, in a sequence required to provide a normal gait for the patient P.

In leg control system 70, the signals from different implantable sensors 72, 74, 76, and 78 require more complex coding, so that sensor/controller 72 can identify which sensor is providing the signals. In addition, the trigger signals from sensor/controller 72 must be coded so that stimulators 80 and 82 can identify the wireless trigger signal to which it will respond.

Figure 5:
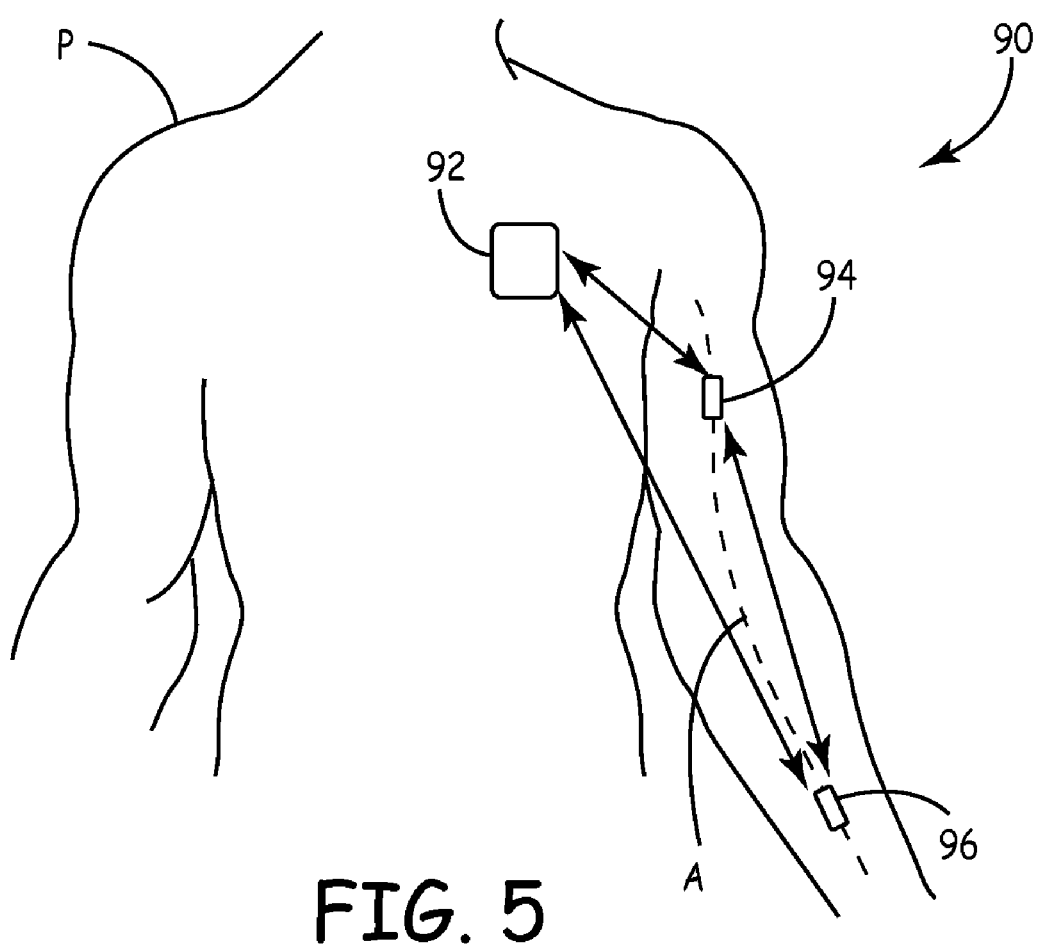
FIG. 5 is a diagram of a telemetry-synchronized arterial monitoring system.

FIG. 5 shows arterial monitoring system 90, which illustrates the use of telemetry-synchronized operation of multiple IMDs in measuring timing differences between pressure measurements made by different IMDs. Arterial monitoring system 90 includes implantable monitor 92 and implantable pressure sensors 94 and 96 located on different segments of the same artery A. When upstream sensor 94 detects a pressure pulse in artery A, it provides a synchronizing trigger to monitor 92 and downstream sensor 96. The wireless trigger allows the downstream sensor 96 to measure time until it detects the same pressure pulse in its segment of artery A. The time difference information can be transmitted to monitor 92, and stored for later transmission.

Alternatively, monitor 92 can provide a trigger to sensors 94 and 96 to cause a time measurement cycle to begin. Sensors 94 and 96, in turn, produce wireless trigger signals upon sensing a pressure pulse in artery A. Monitor 92 measures the time difference between the trigger signal from upstream sensor 94 and the trigger signal from downstream sensor 96. The time differences can be used as a measure of transmission characteristics of the blood vessel to assess hardening of the arteries (i.e. atherosclerosis).

Although the present invention has been described with reference to preferred embodiments, workers skilled in the art will recognize that changes may be made in form and detail without departing from the spirit and scope of the invention.

The invention claimed is:

1. A system of autonomous implantable medical devices, the system comprising:
   a first implantable medical device for interacting with a first region of a body of a patient, the first implantable medical device comprising an ECG monitor;
   a second implantable medical device for interacting with a second region of the body of the patient, the second implantable medical device comprising an EEG monitor;
   an inter-device telemetry link for wirelessly linking the first and second implantable medical devices; and
   a trigger circuit in the first implantable medical device which, when triggered in response to a detected event based on a first physiologic parameter, transmits a trigger signal via the inter-device telemetry link to the second implantable medical device;
   wherein the second implantable medical device initiates storage of data of a second physiological parameter in response to its receipt of the trigger signal, such that the trigger signal causes the second implantable medical device to store data of the second physiological parameter substantially simultaneously with storage of data of the first physiological parameter.

2. The system of claim 1, wherein each of the first and second implantable medical devices stores a clock value based upon the trigger signal.

3. The system of claim 1, wherein the first implantable medical device sends a trigger signal through the telemetry link to the second implantable medical device in response to detection of a cardiac arrhythmia from ECG signals.

4. The system of claim 1, wherein the second implantable medical device sends a trigger signal through the telemetry link to the first implantable medical device in response detecting a seizure from EEG signals.

5. The system of claim 1, wherein the inter-device telemetry link comprises an externally worn relay unit.

6. The system of claim 1 and further comprising an external device for wirelessly signaling at least one of the first and second implantable medical devices to initiate the synchronized action.

7. A system comprising:
   a first implantable device for storing first physiologic signal data, the first implantable device including an internal clock, a transmitter, and a data capture trigger circuit for causing the transmitter to transmit a trigger signal; and
   a second implantable device for storing second physiologic signal data, the second implantable device including a clock, a receiver for receiving trigger signals, wherein the second implantable device, in response to a trigger signal received from the trigger circuit of the first implantable device, records a clock value and the second physiologic signal data,
   wherein the first and second implantable medical devices comprise sensors for sensing arterial pressure at different locations along an artery.

8. The system of claim 7 wherein the first implantable device includes:
   means for detecting a physiologic event based upon the first physiologic signal; and
   means for initiating the trigger signal upon detection of the physiologic event.

9. The system of claim 8 and further comprising an external device for retrieving the first and second physiologic signal data stored by the first and second implantable devices.

10. The system of claim 7 and further comprising an external device for relaying trigger signals between the first and second implantable devices.

11. The system of claim 7 and further comprising an external device for transmitting a signal to the first implantable device to cause the first implantable device to generate the data capture trigger.

12. The system of claim 7, further comprising a third implantable medical device wirelessly linked to the first and second implantable medical devices for measuring transmission characteristics of the artery based on a measured time difference between sensing of an arterial pressure pulse by the first implantable medical device and sensing of the arterial pressure pulse by the second implantable medical device.

13. The system of claim 7, wherein the wearable external device relays the captured data over wireless links to data networks.

14. The system of claim 13, wherein the wearable external device comprises a pager.

15. A system of autonomous implantable medical devices, the system comprising:
   a first implantable medical device for interacting with a first region of a body of a patient;
   a second implantable medical device for interacting with a second region of the body of the patient, wherein the first and second implantable medical devices comprise sensors for sensing arterial pressure at different locations along an artery;
   an inter-device telemetry link for wirelessly linking the first and second implantable medical devices; and
   a trigger circuit in the first implantable medical device which, when triggered in response to a detected event based on a first physiologic parameter, transmits a trigger signal via the inter-device telemetry link to the second implantable medical device;
   wherein the second implantable medical device initiates storage of data of a second physiological parameter in response to its receipt of the trigger signal, such that the trigger signal causes the second implantable medical device to store data of the second physiological parameter substantially simultaneously with storage of data of the first physiological parameter.

16. The system of claim 15 and further comprising:

a third implantable medical device wirelessly linked to the first and second implantable medical devices for storing a measured time difference between sensing of an arterial pressure pulse by the first implantable medical device and sensing of the arterial pressure pulse by the second implantable medical device.

17. The system of claim 15, further comprising a third implantable medical device wirelessly linked to the first and second implantable medical devices for measuring transmission characteristics of the artery based on a measured time difference between sensing of an arterial pressure pulse by the first implantable medical device and sensing of the arterial pressure pulse by the second implantable medical device.

18. A system comprising:

a first implantable device for storing first physiologic signal data, the first implantable device including an internal clock, a transmitter, and a data capture trigger circuit for causing the transmitter to transmit a trigger signal, wherein the first implantable medical device comprises an ECG monitor; and a second implantable device for storing second physiologic signal data, the second implantable device including a clock, a receiver for receiving trigger signals, wherein the second implantable device, in response to the trigger signal received from the trigger circuit of the first implantable device, records a clock value and the second physiologic signal data, wherein the second implantable medical device comprises an EEG monitor.

19. The system of claim 18, wherein the first implantable medical device sends a trigger signal through the telemetry link to the second implantable medical device in response to detection of a cardiac arrhythmia from ECG signals.

20. The system of claim 18, wherein the second implantable medical device sends a trigger signal through the telemetry link to the first implantable medical device in response detecting a seizure from EEG signals.

* * * * *